(12) United States Patent
Kim (10) Patent No.: US 10,646,177 B2
(45) Date of Patent: May 12, 2020

(54) MOBILE X-RAY APPARATUS AND METHOD OF OPERATING THE SAME

(71) Applicant: SAMSUNG ELECTRONICS CO., LTD., Suwon-si (KR)

(72) Inventor: Myeong-je Kim, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 349 days.

(21) Appl. No.: 15/803,036

(22) Filed: Nov. 3, 2017

(65) Prior Publication Data

US 2018/0116614 A1 May 3, 2018

(30) Foreign Application Priority Data

Nov. 3, 2016 (KR) ........................ 10-2016-0145928

(51) Int. Cl.
*A61B 6/00* (2006.01)

(52) U.S. Cl.
CPC .......... *A61B 6/4405* (2013.01); *A61B 6/4283* (2013.01); *A61B 6/4452* (2013.01); *A61B 6/54* (2013.01); *A61B 6/56* (2013.01); *A61B 6/586* (2013.01); *A61B 6/4411* (2013.01); *A61B 6/465* (2013.01); *A61B 6/584* (2013.01)

(58) Field of Classification Search
None
See application file for complete search history.

(56) References Cited

U.S. PATENT DOCUMENTS

| | | | |
|---|---|---|---|
| 8,932,739 | B2 | 1/2015 | Hermann et al. |
| 9,000,718 | B2 | 4/2015 | Park |
| 2015/0054467 | A1 | 2/2015 | Takano et al. |
| 2016/0110242 | A1 | 4/2016 | Kwon et al. |
| 2016/0245874 | A1 | 8/2016 | Kang et al. |

FOREIGN PATENT DOCUMENTS

| | | |
|---|---|---|
| JP | 2013-207901 A | 10/2013 |
| KR | 10-2012-0095608 A | 8/2012 |
| KR | 10-2016-0073109 A | 6/2016 |
| WO | 2015/111987 A1 | 7/2015 |
| WO | 2015/122746 A1 | 8/2015 |

*Primary Examiner* — Edwin C Gunberg
(74) *Attorney, Agent, or Firm* — Sughrue Mion, PLLC (57) ABSTRACT

Provided are a mobile X-ray apparatus for controlling a battery management system (BMS) and a method of operating the mobile X-ray apparatus. The mobile X-ray apparatus may include a power supply that includes a battery and a BMS configured to manage the battery, and a controller configured to control the BMS to shut down in response to detecting a malfunction in the BMS.

18 Claims, 7 Drawing Sheets

MOBILE X-RAY APPARATUS AND METHOD OF OPERATING THE SAME

CROSS-REFERENCE TO RELATED APPLICATION

This application claims priority from Korean Patent Application No. 10-2016-0145928, filed on Nov. 3, 2016, in the Korean Intellectual Property Office, the disclosure of which is incorporated herein in its entirety by reference.

BACKGROUND

1. Field

Apparatuses and methods consistent with example embodiments relate to mobile X-ray apparatuses and methods of operating the same.

2. Description of the Related Art

X-rays, are electromagnetic waves having wavelengths ranging from 0.01 Å to 100 Å, may pass through an object and thus may be widely used in medical devices for imaging the interior of a living body or in nondestructive testing devices of other industries.

An X-ray apparatus using X-rays may obtain an X-ray image of an object by transmitting X-rays emitted from an X-ray source through the object and detecting an intensity difference of the transmitted X-rays by using an X-ray detector. The X-ray apparatus may inspect an internal structure of the object and diagnose the object by using the X-ray image. X-ray apparatuses have advantages in that an internal structure of an object may be easily inspected based on the principle that a transmittance of X-rays varies according to an atomic number of atoms of the object and a density of the object. When a wavelength of X-rays decreases, a transmittance increases and a brightness of the image shown on a screen increases.

SUMMARY

One or more example embodiments provide a mobile X-ray apparatus for controlling a battery management system (BMS) to shut down and a method of operating the mobile X-ray apparatus.

Additional aspects will be set forth in part in the description which follows and, in part, will be apparent from the description, or may be learned by practice of the presented embodiments.

According to an aspect of an example embodiment, a mobile X-ray apparatus may include: a power supply including a battery and a battery management system (BMS) configured to manage the battery; and a controller configured to control the BMS to shut down in response to detecting a malfunction in the BMS.

According to an aspect of an example embodiment, a method of operating a mobile X-ray apparatus including a battery management system (BMS) and a controller may include: detecting a malfunction in the BMS; and controlling the BMS to shut down by using the controller.

According to an aspect of an example embodiment, a computer-readable recording medium may have embodied thereon instructions for executing, via a processor, operations including detecting a malfunction in the battery management system (BMS) of a mobile X-ray apparatus; and controlling the BMS to shut down by using a controller of the mobile X-ray apparatus.

BRIEF DESCRIPTION OF THE DRAWINGS

These and/or other aspects will become apparent and more readily appreciated from the following description of the example embodiments, taken in conjunction with the accompanying drawings in which.

DETAILED DESCRIPTION

Hereinafter, principles and example embodiments of the present disclosure will be described in detail in order to fully convey the scope of the present disclosure and enable one of ordinary skill in the art to embody and practice the present disclosure. The example embodiments may be implemented in various forms.

The same reference numerals denote the same elements throughout the specification. All elements of example embodiments are not described in the specification, and descriptions of matters well known in the art to which the present disclosure pertains or repeated descriptions between example embodiments will not be given. Terms such as "part" and "portion" used herein denote those that may be embodied by software or hardware. According to example embodiments, a plurality of parts or portions may be embodied by a single unit or element, or a single part or portion may include a plurality of elements. Operation principles and example embodiments of the present disclosure will now be explained with reference to the accompanying drawings.

In the present specification, an image may include a medical image obtained by a magnetic resonance imaging (MRI) apparatus, a computed tomography (CT) apparatus, an ultrasound imaging apparatus, an X-ray apparatus, or another medical imaging apparatus.

Furthermore, in the present specification, an "object" may be a target to be imaged and may include a human, an animal, or a part of a human or animal. For example, the object may include a body part (an organ, a tissue, etc.) or a phantom.

Figure 1:
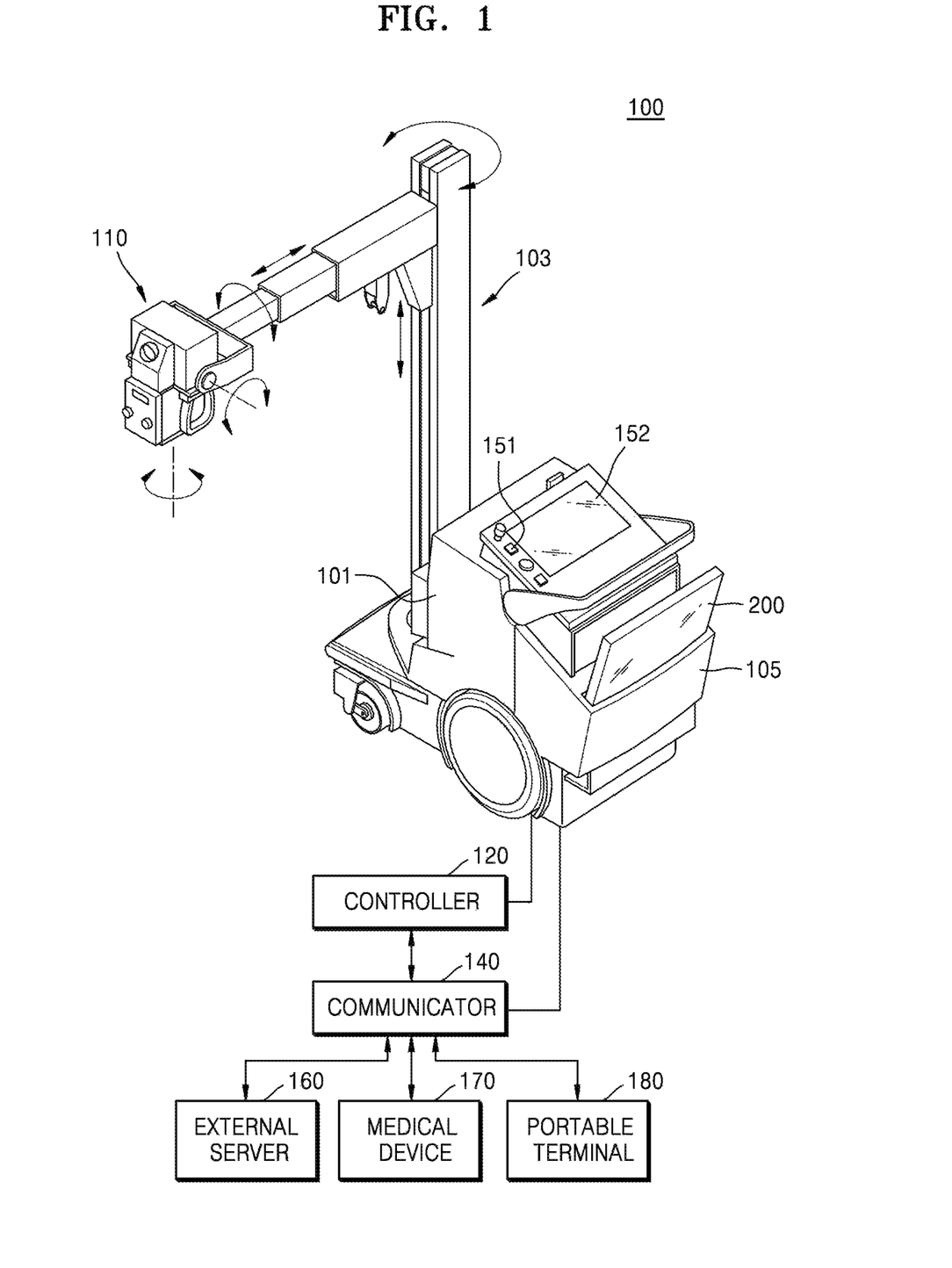
FIG. 1 is a perspective view illustrating an outer appearance of an X-ray apparatus that is a mobile X-ray apparatus.

FIG. 1 is a perspective view illustrating an outer appearance of an X-ray apparatus 100 that is a mobile X-ray apparatus.

Referring to FIG. 1, the X-ray apparatus 100 includes an X-ray emitter 110 configured to generate and emit X-rays, an input interface 151 configured to receive a command from a user, a display 152 configured to provide information to the user, a controller 120 configured to control the X-ray apparatus 100 according to the command, and a communicator 140 configured to communicate with an external device.

The X-ray emitter 110 may include an X-ray source for generating X-rays, and a collimator for adjusting a radiation field of X-rays generated by the X-ray source.

When the X-ray apparatus 100 is a mobile X-ray apparatus, since a main body 101 to which the X-ray emitter 110 is connected may freely move and an arm 103 for connecting the X-ray emitter 110 to the main body 101 may also rotate and linearly move, the X-ray emitter 110 may freely move in a three-dimensional (3D) space.

The input interface 151 may receive a command for controlling a position of the X-ray emitter 110, an imaging timing, an imaging condition, or an imaging protocol. The input interface 151 may include a keyboard, a mouse, a touchscreen, and/or a speech recognizer.

The display 152 may display a screen for guiding a user input, an X-ray image, and/or a screen showing a state of the X-ray apparatus 100.

The controller 120 may control an imaging timing and an imaging condition of the X-ray emitter 110 according to a control command input from the user, and may generate a medical image by using image data received from an X-ray detector 200. Also, the controller 120 may control a position or an attitude (i.e., orientation) of the X-ray emitter 110 according to a position of an object P and an imaging protocol.

The controller 120 may include a memory in which a program for performing operations described above and below is stored and a processor for executing the stored program. The controller 120 may include a single processor or a plurality of processors. When the controller 120 includes a plurality of processors, the plurality of processors may be integrated into one chip or may be physically separated from one another.

A storage 105 for storing the X-ray detector 200 may be provided on the main body 101. Also, a charging terminal for charging the X-ray detector 200 may be provided in the storage 105. Accordingly, the X-ray detector 200 may be charged while being stored in the storage 105.

The input interface 151, the display 152, the controller 120, and the communicator 140 may be provided in the main body 101. Image data obtained by the X-ray detector 200 may be transmitted to the main body 101 to be processed, and then may be displayed on the display 152 or transmitted to an external device through the communicator 140.

Also, the controller 120 and the communicator 140 may be physically separated from the main body 101, or some elements of the controller 120 and the communicator 140 may be provided in the main body 101.

The X-ray apparatus 100 may be connected to an external device, such as an external server 160, a medical device 170, and/or a portable terminal 180 (e.g., a smartphone, a tablet personal computer (PC), or a wearable device), through the communicator 140 and may transmit or receive data to or from the external device.

The communicator 140 may include one or more elements that may perform communication with the external device, and may include at least one from among, for example, a short-range communication module, a wired communication module, and a wireless communication module.

Alternatively, the communicator 140 may receive a control signal from the external device and may transmit the received control signal to the controller 120, and the controller 120 may control the X-ray apparatus 100 according to the received control signal.

Also, the controller 120 may transmit a control signal to the external device through the communicator 140 and may control the external device according to the control signal of the controller 120. For example, the external device may process data of the external device according to the control signal of the controller 120 received through the communicator 140.

Also, the communicator 140 may further include an internal communication module for performing communication between elements of the X-ray apparatus 100. A program for controlling the X-ray apparatus 100 may be installed in the external device, and may include a command for performing some or all of operations of the controller 120.

The program may be previously installed in the portable terminal 180, or may be downloaded by a user of the portable terminal 180 from a server that provides an application and then may be installed. The server that provides the application may include a computer-readable recording medium in which the program is stored.

Also, the communicator 140 may further include an internal communication module for performing communication between elements of the X-ray apparatus 100.

Figure 2:
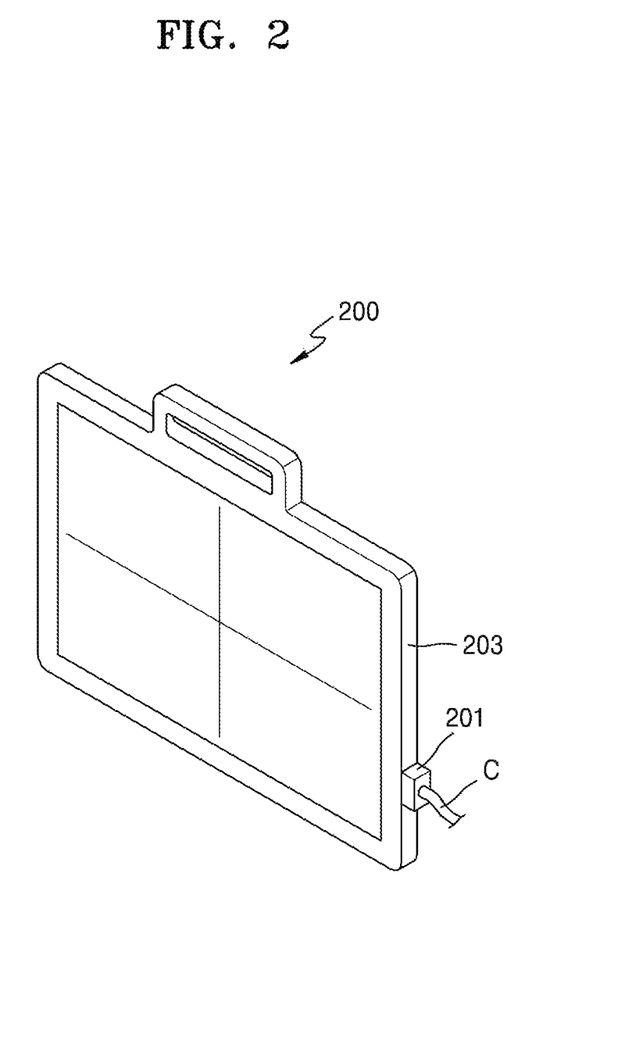
FIG. 2 is a perspective view illustrating an outer appearance of an X-ray detector.

FIG. 2 is a perspective view illustrating an outer appearance of the X-ray detector 200.

As described above, the X-ray detector 200 used in the X-ray apparatus 100 may be implemented as a portable X-ray detector. The X-ray detector 200 may be equipped with a battery for supplying power to operate wirelessly (e.g., cordlessly), or as shown in FIG. 2, may operate by connecting a charge port 201 to a separate power supply via a cable C.

A case 203 forms an outer appearance and shape of the X-ray detector 200 and has therein a plurality of detecting elements for detecting X-rays and converting the X-rays into image data, a memory for temporarily or permanently storing the image data, a communication module for receiving a control signal from the X-ray apparatus 100 or transmitting the image data to the X-ray apparatus 100, and a battery. Further, image correction information and intrinsic identification (ID) information of the X-ray detector 200 may be stored in the memory, and the stored ID information may be transmitted together with the image data during communication with the X-ray apparatus 100.

Figure 3:
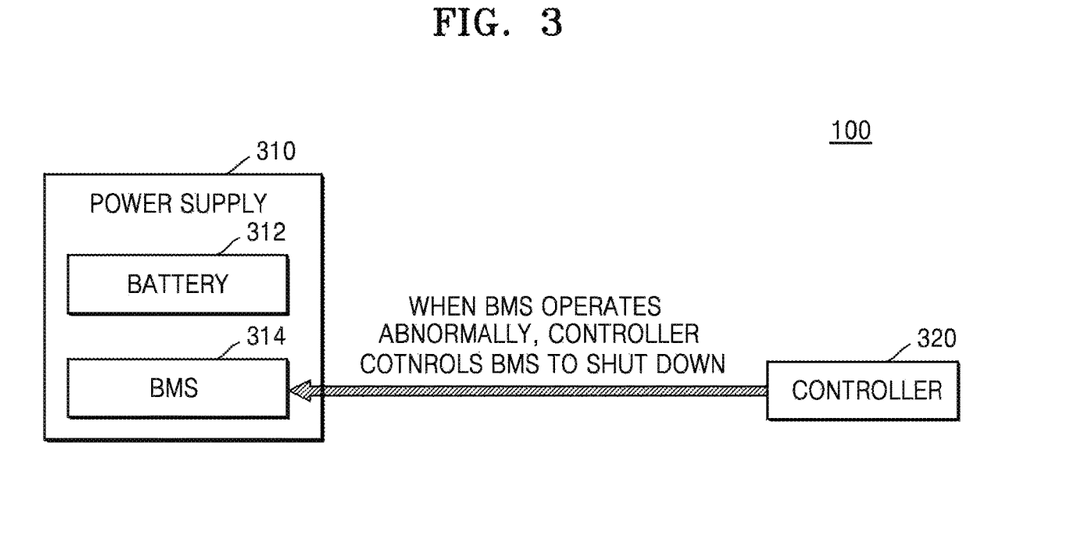
FIG. 3 is a block diagram of the X-ray apparatus according to an example embodiment.

FIG. 3 is a block diagram of the X-ray apparatus 100 according to an example embodiment.

The X-ray apparatus 100 may include a power supply 310 and a controller 320. The X-ray apparatus 100 of FIG. 3 may be a mobile X-ray apparatus like in FIG. 1, and only elements related to the present example embodiment are illustrated. Accordingly, it will be understood by one of ordinary skill in the art that elements other than the elements illustrated in FIG. 3 may be further included.

The power supply 310 may include a battery 312 and a battery management system (BMS) 314.

The battery 312 may supply operating power to elements of the X-ray apparatus 100 that require operating power. For example, the battery 312 may supply operating power not only to the BMS 314 and the controller 320 but also to the input interface 151, the display 152, and the communicator 140 of the X-ray apparatus 100.

According to an example embodiment, the battery 312 may be a rechargeable battery. For example, the battery 312 may be a lithium-ion battery having a structure in which a plurality of battery cells are connected and coupled to one another.

The BMS 314 may detect a state (e.g., a voltage or a temperature) of the battery 312. The BMS 314 may control and manage the power supply 310 based on the state of the battery 312. The BMS 314 may include a protection circuit for preventing the battery 312 from being damaged based on the state of the battery 312. According to an example embodiment, the BMS 314 may shut down when the battery 312 is in an unsafe condition, such as overdischarge, overcurrent, overheat, and/or charge imbalance between batteries. For example, the BMS 314 itself may shut down by triggering the shutdown circuit.

When it is determined that the battery 312 is in an unsafe condition, the BMS 314 may generate a shutdown ready signal and then block (e.g., disconnect) a charging path and a discharging path of the battery 312. Also, the BMS 314 may shut down within a predetermined period of time after the shutdown ready signal is generated. According to an example embodiment, the BMS 314 may shut down within a predetermined period of time after the BMS 314 transmits the shutdown ready signal to the controller 320.

The power supply 310 and the controller 320 may each include a communication interface (also referred to as a "communicator") to communicate with each other. For example, the controller 320 may receive the shutdown ready signal from the BMS 314 through controller area network (CAN) communication. Also, each of the power supply 310 and the controller 320 may be configured as a separate modular unit.

The controller 320 may detect that the BMS 314 operates abnormally (e.g., malfunctions), and may control the BMS 314 to shut down.

The controller 320 may control the BMS 314 to shut down when the BMS 314 does not properly block the charging path and the discharging path of the battery 312 even after the shutdown ready signal is generated. In detail, when the BMS 314 operates normally, the BMS 314 may generate the shutdown ready signal and then may block the charging path of the battery 312, and thus power supply to the controller 320 may be cut off. Accordingly, the controller 320 may be turned off due to power off. However, when the BMS 314 operates abnormally (e.g., outside the normal parameters), even after the BMS 314 generates the shutdown ready signal, the BMS 314 may fail to block the discharging path of the battery 312 as expected. Accordingly, when the controller 320 is not turned off within a predetermined period of time after the BMS 314 generates the shutdown ready signal, the controller 320 may determine that the BMS 314 is operating abnormally and then control the BMS 314 to shut down.

When the BMS 314 does not shut down within a predetermined period of time after the shutdown ready signal is generated, the controller 320 may control the BMS 314 to shut down. In detail, when the BMS 314 operates normally, the BMS 314 itself may shut down within a predetermined period of time after the shutdown ready signal is generated, and thus power supply to the controller 320 may be cut off. Accordingly, the controller 320 may be turned off due to power off. However, when the BMS 314 operates abnormally, even though the BMS 314 generates the shutdown ready signal, the BMS 314 itself may not shut down within a predetermined period of time. Accordingly, when the controller 320 is not turned off within a predetermined period of time after the BMS 314 generates the shutdown ready signal, the controller 320 may determine that the BMS 314 operates abnormally and then may control the BMS 314 to shut down.

Also, when the BMS 314 does not shut down within a predetermined period of time after the BMS 314 generates the shutdown ready signal, the controller 320 may operate in a power-off mode. The power-off mode may be also referred to as a low-power mode, a power save mode, a sleep mode, etc. While in the power-off mode, the controller 320 may maintain power supply only to those modules that require regular power (e.g., the same voltage level as when the controller 320 is operating under a non-power-saving mode), and may cut off power supply to other modules. Accordingly, the controller 320 may be the only load of the power supply 310 in the power-off mode. Next, the controller 320 may control the BMS 314 to shut down in the power-off mode. In detail, the controller 320 may control the BMS 314 to shut down and only allow the use of modules that require regular power, in the power-off mode. Also, the controller 320 may operate in the power-off mode, and may control the BMS 314 to shut down after a predetermined period of time elapses. Even though the BMS 314 is controlled to shut down, a reverse current may flow into the BMS 314 due to charges stored in capacitance components (e.g., capacitors) of the controller 320 to restart the BMS 314. In order to prevent this problem, the controller 320 may first operate in the power-off mode (e.g., a minimum load state) before shutting down the BMS 314, and after a predetermined period of time elapses, may control the BMS 314 to shut down.

Also, the controller 320 may include a discharge resistor. The controller 320 may discharge the charges stored in the capacitance components of the controller 320 by using the discharge resistor. In other words, the controller 320 may enable current due to the charges stored in the capacitance components of the controller 320 to flow through the discharge resistor. Also, when the BMS 314 does not shut down within a predetermined period of time after the shutdown ready signal is generated, the controller 320 may operate in the power-off mode, wait for a predetermined period of time to discharge the charges stored in the capacitance components of the controller 320 by using the discharge resistor, and then control the BMS 314 to shut down.

When it is determined that communication with the BMS 314 is abnormal, the controller 320 may control the BMS 314 to shut down. For example, the controller 320 may try to communicate with the BMS 314. When the controller 320 fails to communicate with the BMS 314, the controller 320 may determine that communication with the BMS 314 is abnormal, and may control the BMS 314 to shut down.

Also, when the controller 320 determines that communication with the BMS 314 is abnormal and the power supply 310 is overheated, the controller 320 may control the BMS 314 to shut down. According to an example embodiment, the power supply 310 may include a temperature sensor that may be directly monitored by the controller 320. Accordingly, the controller 320 may obtain temperature information of the power supply 310 by using the temperature sensor. Next, when the controller 320 determines that the power supply 310 is overheated based on the obtained temperature information and communication with the BMS 314 is abnormal, the controller 320 may control the BMS 314 to shut down. For example, when a temperature of the power supply 310 is greater than or equal to a threshold value, the controller 320 may determine that the power supply 310 is overheated.

The power supply 310 may include an interrupt pin that may be directly controlled by the controller 320. The controller 320 may control the BMS 314 to shut down by using the interrupt pin included in the power supply 310. The controller 320 may control the BMS 314 to shut down by operating a shutdown circuit of the power supply 310 by using the interrupt pin. Also, the controller 320 may control the BMS 314 to shut down by cutting off power supply to the BMS 314 from the battery 312 by using the interrupt pin.

Accordingly, since the X-ray apparatus 100 may shut down the BMS 314 by using the controller 320 when the BMS 314 operates abnormally, the X-ray apparatus 100 may protect the battery 310 more safely. In particular, since the X-ray apparatus 100 may shut down the BMS 314 under the control of the controller 320 just in case the BMS 314 does not appropriately block the charging path and the discharging path of the battery 312 and the BMS 314 itself does not shut down, the X-ray apparatus 100 may provide 3-way protection for the battery 312.

Figure 4:
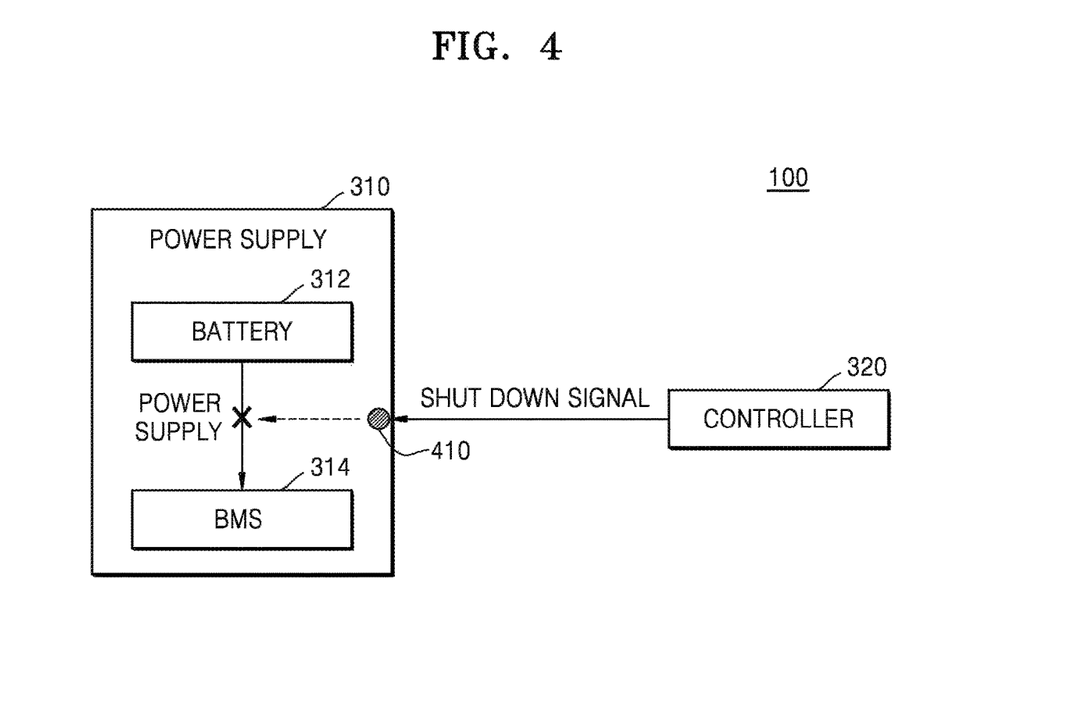
FIG. 4 is a diagram illustrating an example where a controller controls a battery management system (BMS) to shut down by using an interrupt pin according to an example embodiment.

FIG. 4 is a diagram illustrating an example where the controller 320 controls the BMS 314 to shut down by using an interrupt pin 410 according to an example embodiment.

The power supply 310 may include the interrupt pin 410 that may be directly controlled by the controller 320. The controller 320 may control the BMS 314 to shut down by using the interrupt pin 410.

In detail, the controller 320 may input a shut down signal to the power supply 310 through the interrupt pin 410, and the power supply 310 may cut off power supply to the BMS 314 from the battery 312 based on the shut down signal. For example, when the power supply 310 receives the shut down signal from the controller 320, the power supply 310 may cut off power supply to the BMS 314 from the battery 312 by turning off a field-effect transistor (FET). Accordingly, the BMS 314 may shut down, and thus a charging path and a discharging path of the battery 312 may be blocked.

Figure 5:
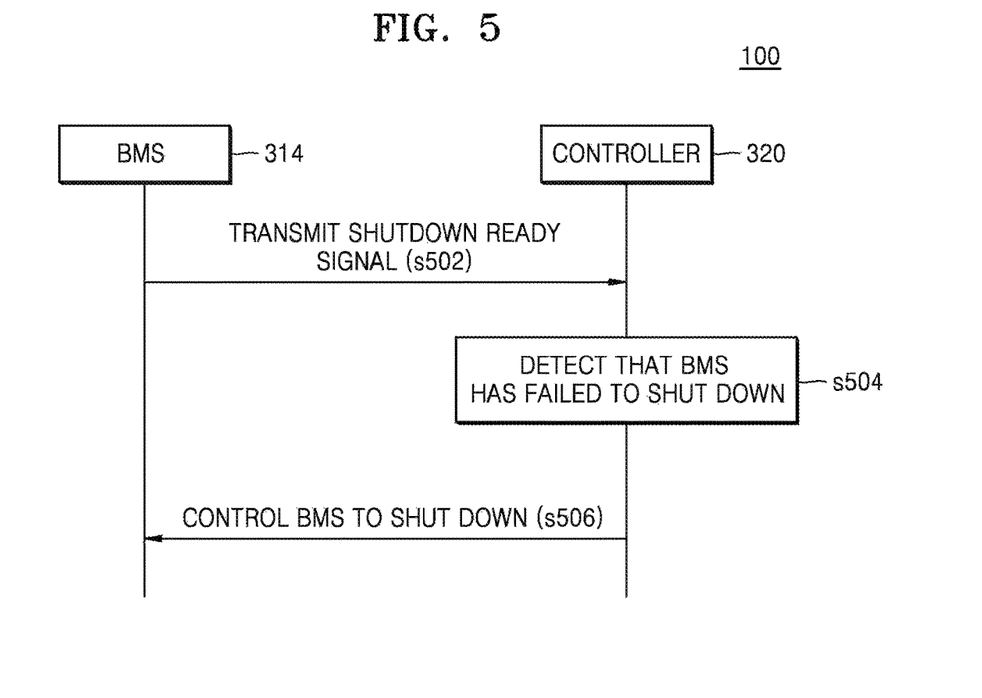
FIG. 5 is a diagram illustrating an example where the controller shuts down the BMS when the BMS operates abnormally, according to an example embodiment.

FIG. 5 is a diagram illustrating an example where the controller 320 shuts down the BMS 314 when the BMS 314 is abnormal according to an example embodiment.

In operation s502, the BMS 314 may transmit a shutdown ready signal to the controller 320. When the battery 312 is in an unsafe condition, such as overdischarge, overcurrent, overheat, and charge imbalance between batteries, the BMS 314 may generate the shutdown ready signal and may transmit the shutdown ready signal to the controller 320. For example, the BMS 314 may transmit the shutdown ready signal to the controller 320 through CAN communication.

In operation s504, the controller 320 may detect that the BMS 314 has failed to shut down. When the controller 320 is not turned off within a predetermined period of time after the controller 320 receives the shutdown ready signal, it may be determined that the BMS 314 is not able to shut down on its own. For example, the controller 320 may activate a timer at a point of time when the controller 320 receives the shutdown ready signal, and when the controller 320 is not turned off three minutes after the timer is activated, the controller 320 may determine that the BMS 314 has failed to shut down.

Also, when the controller 320 is not turned off within a predetermined period of time after the controller 320 receives the shutdown ready signal, the controller 320 may determine that the BMS 314 has failed to block (e.g., disconnect) a charging path and a discharging path of the battery 312.

In operation s506, the controller 320 may control the BMS 314 to shut down. According to an example embodiment, the controller 320 may control the BMS 314 to shut down by using an interrupt pin included in the power supply 310.

Figure 6:
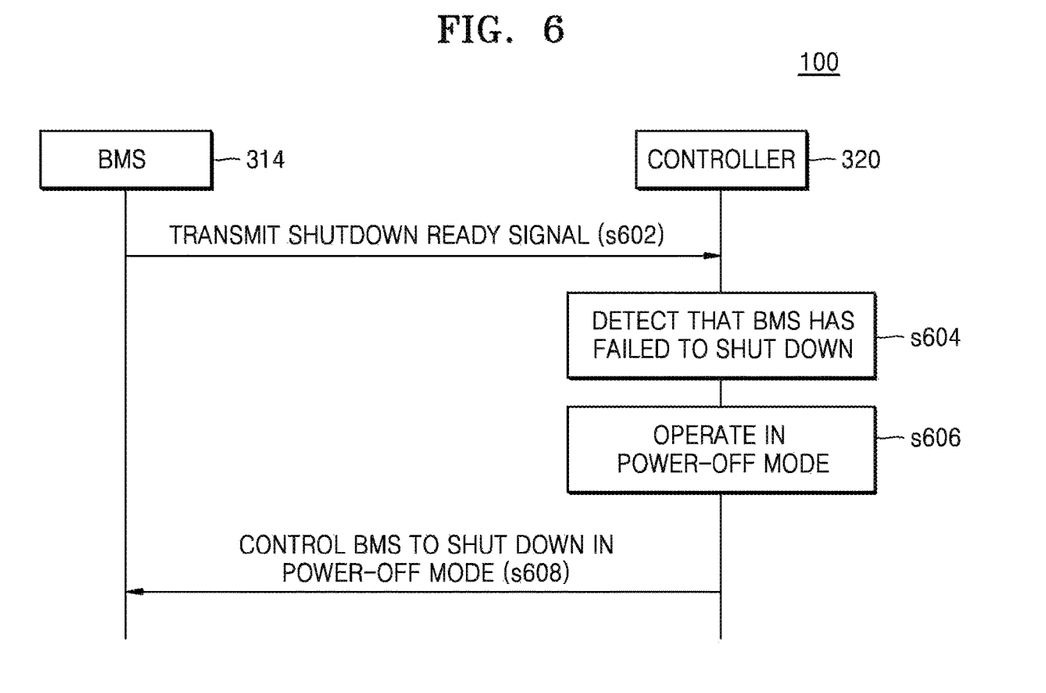
FIG. 6 is a diagram illustrating an example where the controller shuts down the BMS when the BMS operates abnormally, according to an example embodiment.

FIG. 6 is a diagram illustrating an example where the controller 320 shuts down the BMS 314 when the BMS 314 is abnormal according to an example embodiment.

In operation s602, the BMS 314 may transmit a shutdown ready signal to the controller 320.

In operation s604, the controller 320 may detect that the BMS 314 has failed to shut down. Also, the controller 320 may detect that the BMS 314 has failed to block a charging path and a discharging path.

In operation s606, the controller 320 may operate in a power-off mode. In other words, the controller 320 may operate only some modules that require regular power by cutting off power to other modules.

In operation s608, the controller 320 may control the BMS 314 to shut down, in the power-off mode. The controller 320 may control the BMS 314 to shut down by using the module that operates with regular power. Also, the controller 320 may control the BMS 314 to shut down after waiting for a predetermined period of time in the power-off mode.

Figure 7:
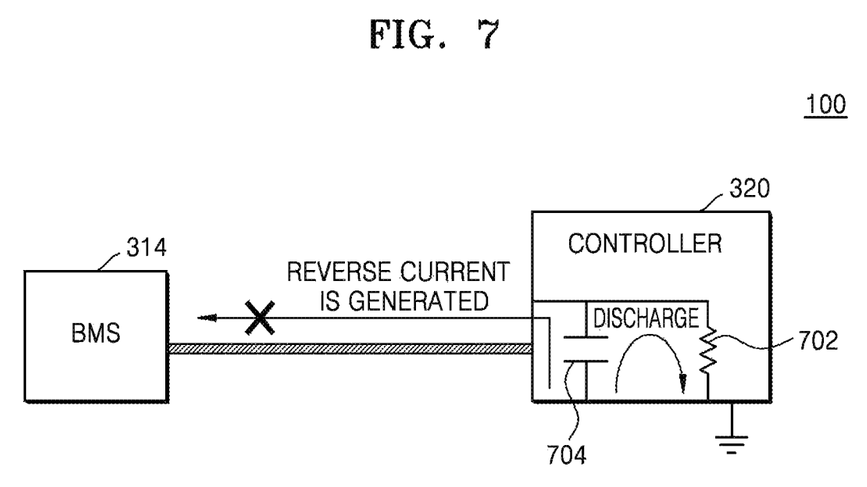
FIG. 7 is a diagram illustrating an example where the controller includes a discharge resistor, according to an example embodiment.

FIG. 7 is a diagram illustrating an example where the controller 320 includes a discharge resistor 702 according to an example embodiment.

The controller 320 may include the discharge resistor 702. The discharge resistor 702 may discharge charges stored in a capacitance component 704 in the controller 320. In detail, even when the controller 320 shuts down the BMS 314, reverse current due to the charges stored in the capacitance component 704 in the controller 320 may flow into the BMS 314 through a power line, and thus the BMS 314 that has already shut down may be restarted. Accordingly, the controller 320 may include the discharge resistor 702 for preventing reverse current, and may discharge the charges stored in the capacitance component 704 in the controller 320 by using the discharge resistor 702.

Figure 8:
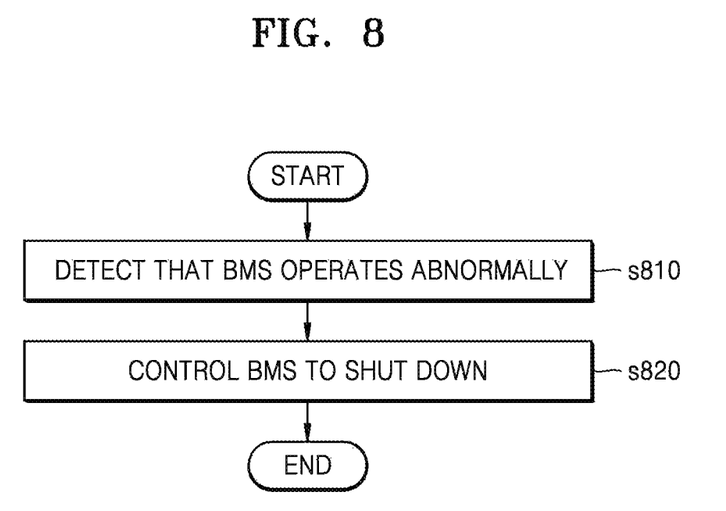
FIG. 8 is a flowchart of a method of operating the X-ray apparatus, according to an example embodiment.

FIG. 8 is a flowchart of a method of operating the X-ray apparatus 100 according to an example embodiment.

The method of FIG. 8 may be performed by elements of the X-ray apparatus 100 of any of FIGS. 1 and 3 through 7, and a repeated explanation will not be given.

In operation s810, the X-ray apparatus 100 may detect that a BMS operates abnormally. According to an example embodiment, when the BMS does not block a charging path and a discharging path of a battery after a shutdown ready signal is generated, the X-ray apparatus 100 may determine that the BMS abnormally operates. In other words, the X-ray apparatus 100 may detect a malfunction in the BMS. Also, when the BMS does not shut down on its own after the shutdown ready signal is generated, the X-ray apparatus 100 may determine that the BMS operates abnormally. According to another example embodiment, when communication between a controller and the BMS fails, the X-ray apparatus 100 may determine that the BMS operates abnormally.

When the X-ray apparatus 100 detects that the BMS operates abnormally, the method proceeds to operation s820. In operation s820, the X-ray apparatus 100 may control the BMS to shut down by using the controller. According to an example embodiment, the X-ray apparatus 100 may control the BMS to shut down by cutting off power supply to the BMS by using an interrupt pin included in a power supply.

Figure 9:
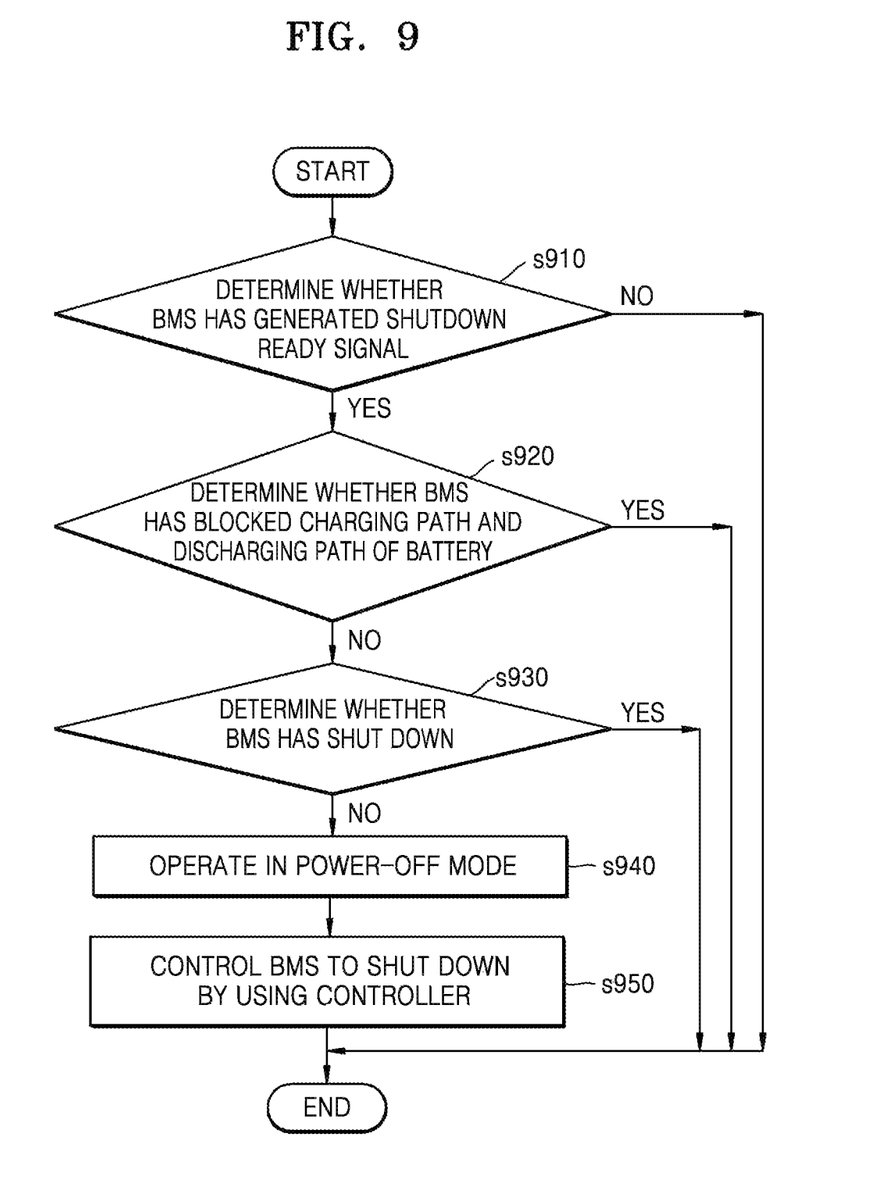
FIG. 9 is a flowchart of a method of operating the X-ray apparatus, according to an example embodiment.

FIG. 9 is a flowchart of a method of operating the X-ray apparatus 100 according to an example embodiment.

The method of FIG. 9 may be performed by elements of the X-ray apparatus 100 of any of FIGS. 1 and 3 through 7, and a repeated explanation will not be given.

In operation s910, the X-ray apparatus 100 may determine whether a BMS has generated a shutdown ready signal.

When the X-ray apparatus 100 determines in operation s910 that the BMS generates the shutdown ready signal, the method proceeds to operation s920. In operation s920, the X-ray apparatus 100 may determine whether the BMS has blocked a charging path and a discharging path of a battery. According to an embodiment, the X-ray apparatus 100 may determine that the BMS does not block the charging path and the discharging path of the battery when a controller is not turned off within a predetermined period of time after the shutdown ready signal is generated. For example, when the controller is not turned off within 1 minute after the shutdown ready signal is generated, the X-ray apparatus 100 may determine that the BMS has failed to block the charging path and the discharging path of the battery. In contrast, when the controller is turned off within a predetermined period of time after the shutdown ready signal is generated, the X-ray apparatus 100 may determine that the BMS has successfully blocked the charging path and the discharging path of the battery.

When the X-ray apparatus 100 determines in operation s920 that the BMS has not blocked the charging path and the discharging path of the battery, the method proceeds to operation s930. In operation s930, the X-ray apparatus 100 may determine whether the BMS has shut down. According to an example embodiment, when the controller is not turned off within a predetermined period of time after the shutdown ready signal is generated, the X-ray apparatus 100 may determine that the BMS has failed to shut down. For example, when the controller is not turned off within 3 minutes after the shutdown ready signal is generated, the X-ray apparatus 100 may determine that the BMS has failed to shut down on its own. In contrast, when the controller is turned off within a predetermined period of time after the shutdown ready signal is generated, the X-ray apparatus 100 may determine that the BMS has successfully shut down.

In operation s940, the X-ray apparatus 100 may operate in a power-off mode. For the power-off mode, the X-ray apparatus 100 may maintain power supply to only some modules that require regular power and may cut off power supply to other modules.

In operation s950, the X-ray apparatus 100 may control the BMS to shut down by using the controller. Also, the X-ray apparatus 100 may control the BMS to shut down by using the module that operates with regular power in the controller, in the power-off mode. Also, the X-ray apparatus 100 may wait for a predetermined period of time in the power-off mode, and then may discharge charges remaining in the controller by using a discharge resistor.

Accordingly, since the X-ray apparatus 100 may control the BMS to shut down by using the controller just in case the BMS fails to block the charging path and the discharging path of the battery and the BMS also fails to shut down, the X-ray apparatus 100 may provide 3-way fail-safe protection for the battery with redundancy.

Figure 10:
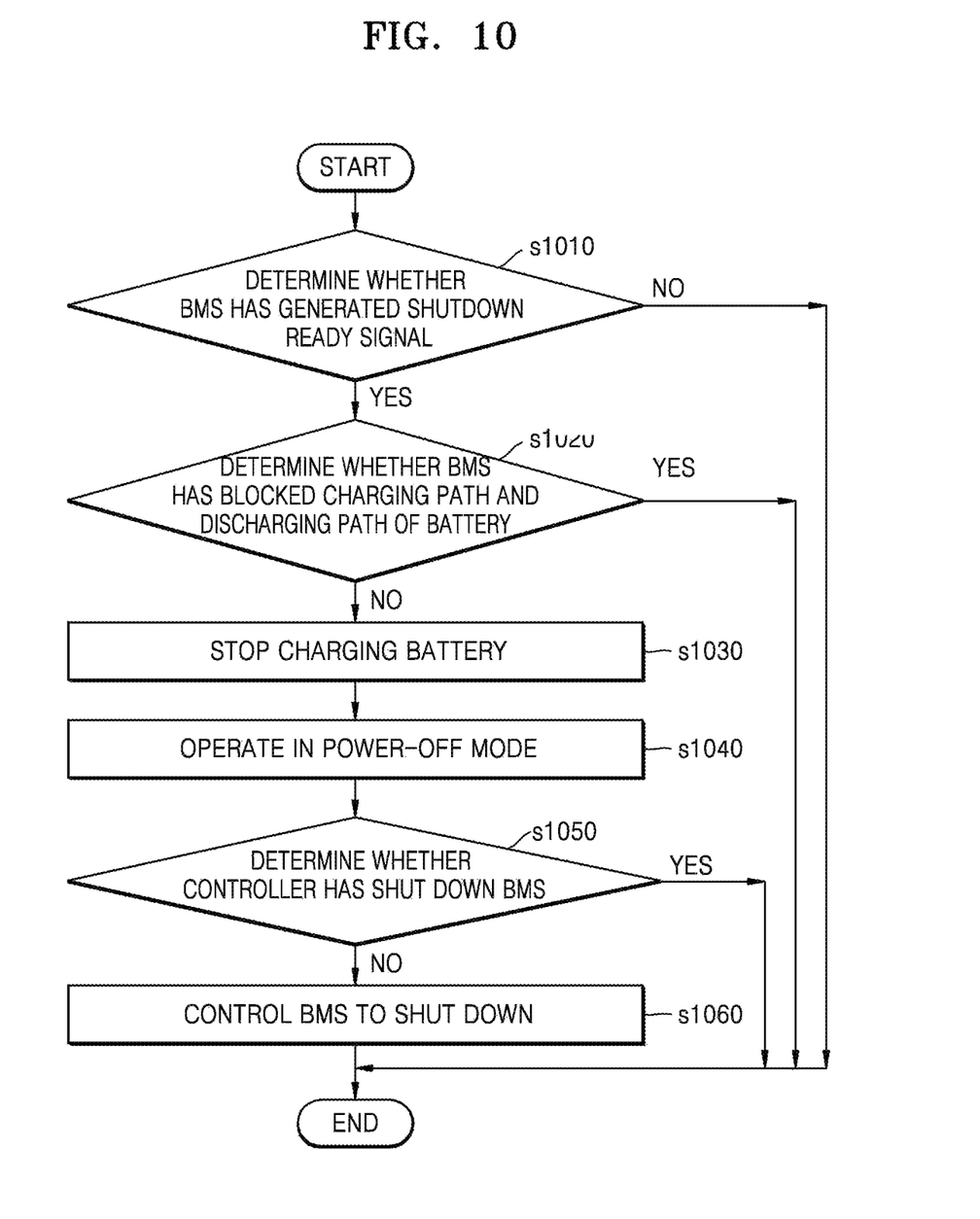
FIG. 10 is a flowchart of a method of operating the X-ray apparatus, according to an example embodiment.

FIG. 10 is a flowchart of a method of operating the X-ray apparatus 100 according to an example embodiment.

The method of FIG. 10 may be performed by elements of the X-ray apparatus 100 of any of FIGS. 1 and 3 through 7, and a repeated explanation will not be given.

In operation s1010, the X-ray apparatus 100 may determine whether a BMS has generated a shutdown ready signal.

When the X-ray apparatus 100 determines in operation s1010 that the BMS has generated the shutdown ready signal, the method proceeds to operation s1020. In operation s1020, the X-ray apparatus 100 may determine whether the BMS has blocked a charging path and a discharging path of a battery.

When the X-ray apparatus 100 determines in operation s1020 that the BMS has not blocked the charging path and the discharging path of the battery, the method proceeds to operation s1030. In operation s1030, the X-ray apparatus 100 may stop charging the battery. In detail, the X-ray apparatus 100 may stop a charging operation of a charger by using a controller. Also, the X-ray apparatus 100 may wait for a predetermined period of time after stopping charging the battery. For example, the X-ray apparatus 100 may wait for about 1 minute after stopping charging the battery.

In operation s1040, the X-ray apparatus 100 may operate in a power-off mode. Also, the X-ray apparatus 100 may wait for a predetermined period of time after operating in the power-off mode. For example, the X-ray apparatus 100 may wait for 1 minute after operating in the power-off mode.

In operation s1050, the X-ray apparatus 100 may determine whether the controller has shut down the BMS.

When the X-ray apparatus 100 determines in operation s1050 that the controller has not shut down the BMS, the method proceeds to operation s1060. In operation s1060, the X-ray apparatus 100 may control the BMS to shut down. Also, when the controller does not shut down the BMS, the X-ray apparatus 100 may wait for a predetermined period of time and then may control the BMS to shut down. For example, when the controller does not shut down the BMS, the X-ray apparatus 100 may wait for about 3 minutes and then may control the BMS itself to shut down.

Accordingly, since the X-ray apparatus 100 may control the BMS to shut down just in case the BMS fails to block the charging path and the discharging path of the battery and the controller also fails to shut down the battery, the X-ray apparatus 100 may provide 3-way protection for the battery.

The device described herein may include a processor, a memory for storing and executing program data, permanent storage such as a disk drive, a communications port for handling communications with external devices, and user interface devices, including a touch panel, keys, buttons, etc. When software modules or algorithms are involved, these software modules may be stored as program instructions or computer-readable codes executable on a processor on a computer-readable medium. Examples of the computer-readable recording medium include magnetic storage media (e.g., read-only memories (ROMs), random-access memories (RAMs), floppy disks, hard disks, etc.), and optical recording media (e.g., compact disc (CD)-ROMs, or digital versatile discs (DVDs)). The computer-readable recording medium may also be distributed over network coupled computer systems so that the computer-readable code is stored and executed in a distributive manner. This medium may be read by the computer, stored in the memory, and executed by the processor.

The present disclosure may be described in terms of functional block components and various processing steps. Such functional blocks may be realized by any number of hardware and/or software components configured to perform the specified functions. For example, the present disclosure may employ various integrated circuit (IC) components, e.g., memory elements, processing elements, logic elements, look-up tables, and the like, which may carry out a variety of functions under the control of one or more microprocessors or other control devices. Similarly, where the elements of the present disclosure are implemented using software programming or software elements, the disclosure may be implemented with any programming or scripting language such as C, C++, Java, assembler language, or the like, with the various algorithms being implemented with any combination of data structures, objects, processes, routines or other programming elements. Functional aspects may be implemented in algorithms that are executed on one or more processors. Furthermore, the present disclosure could employ any number of conventional techniques for electronics configuration, signal processing and/or control, data processing and the like. The words "mechanism," "element," "means," and "configuration" are used broadly and are not limited to mechanical or physical embodiments, but may include software routines in conjunction with processors, etc.

What is claimed is:

1. A mobile X-ray apparatus comprising:
a power supply comprising a battery and a battery management system (BMS) configured to manage the battery; and
a controller configured to control the BMS to be shut down in response to detecting a malfunction in the BMS.

2. The mobile X-ray apparatus of claim 1, wherein the power supply further comprises an interrupt pin directly controllable by the controller,
wherein the controller is further configured to control the BMS to be shut down by using the interrupt pin to cut off power being supplied to the BMS from the battery.

3. The mobile X-ray apparatus of claim 1, wherein the controller is further configured to control the BMS to be shut down when the BMS does not shut down within a predetermined period of time after a shutdown ready signal is generated by the BMS.

4. The mobile X-ray apparatus of claim 1, wherein the controller is further configured to operate in a power-off mode when the controller detects the malfunction in the BMS, and
wherein the controller is further configured to control the BMS to be shut down by using a module configured to operate with regular power in the power-off mode.

5. The mobile X-ray apparatus of claim 4, wherein the controller comprises a discharge resistor, and
wherein the controller is further configured to discharge charges remaining in the controller by using the discharge resistor, in the power-off mode.

6. The mobile X-ray apparatus of claim 1, wherein the controller is further configured to control the BMS to be shut down in response to the controller being unable to communicate with the BMS.

7. The mobile X-ray apparatus of claim 1, wherein the power supply further comprises a temperature sensor directly monitored by the controller, and
wherein the controller is further configured to obtain temperature information of the power supply by using the temperature sensor and to control the BMS to be shut down in response to the controller determining that a temperature of the power supply is greater than or equal to a threshold value based on the temperature information and the controller being unable to communicate with the BMS.

8. The mobile X-ray apparatus of claim 1, wherein the controller is further configured to control the BMS to be shut down in response to the BMS not blocking a charging path and a discharging path of the battery within a predetermined period of time after a shutdown ready signal is generated.

9. The mobile X-ray apparatus of claim 1, wherein the battery is a lithium-ion battery.

10. A method of operating a mobile X-ray apparatus comprising a battery management system (BMS) and a controller, the method comprising:
detecting a malfunction in the BMS; and
controlling the BMS to be shut down by using the controller.

11. The method of claim 10, wherein the controlling comprises controlling the BMS to be shut down by cutting off power being supplied to the BMS.

12. The method of claim 10, wherein the detecting comprises detecting that the BMS does not shut down within a predetermined period of time after a shutdown ready signal is generated.

13. The method of claim 10, wherein the controlling comprises:
operating in a power-off mode; and
controlling the BMS to be shut down by using a module configured to operate with regular power in the power-off mode.

14. The method of claim 13, wherein the controlling further comprises discharging charges remaining in the controller by using a discharge resistor, in the power-off mode.

15. The method of claim 10, wherein the detecting comprises detecting that the controller is unable to communicate with the BMS.

16. The method of claim 10, wherein the detecting comprises detecting that a temperature of a power supply is greater than or equal to a threshold value and the controller is unable to communicate with the BMS.

17. The method of claim 10, wherein the detecting comprises detecting that the BMS has not blocked a charging path and a discharging path of a battery within a predetermined period of time after a shutdown ready signal is generated.

18. A computer-readable recording medium having embodied thereon instructions for executing, via a processor, operations comprising:
detecting a malfunction in a battery management system (BMS) of a mobile X-ray apparatus; and
controlling the BMS to be shut down by using a controller of the mobile X-ray apparatus.

* * * * *